US009410884B2

(12) United States Patent
Morita et al.

(10) Patent No.: US 9,410,884 B2
(45) Date of Patent: Aug. 9, 2016

(54) COMPONENT MEASUREMENT DEVICE

(75) Inventors: Takashi Morita, Ashigarakami-gun (JP); Yasushi Nagasawa, Ashigarakami-gun (JP); Masami Murayama, Tokorozawa (JP); Yoshio Nagaoka, Kamagaya (JP); Eiki Izumi, Taito-ku (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days.

(21) Appl. No.: 13/824,017

(22) PCT Filed: Jul. 19, 2011

(86) PCT No.: PCT/JP2011/066371
§ 371 (c)(1),
(2), (4) Date: Mar. 15, 2013

(87) PCT Pub. No.: WO2012/043023
PCT Pub. Date: Apr. 5, 2012

(65) Prior Publication Data
US 2013/0177479 A1    Jul. 11, 2013

(30) Foreign Application Priority Data

Sep. 30, 2010   (JP) .................................. 2010-223067

(51) Int. Cl.
*G01N 21/00*    (2006.01)
*G01N 21/01*    (2006.01)
(Continued)

(52) U.S. Cl.
CPC ............ *G01N 21/55* (2013.01); *G01N 21/8483* (2013.01); *B65H 2513/40* (2013.01);
(Continued)

(58) Field of Classification Search
CPC ..................... B65H 2513/40; B65H 2553/414; G01N 21/55; G01N 21/6456; G01N 21/6486; G01N 15/1434; G01N 21/0303; G01N 21/31; G01N 15/1459; G01N 15/1463; G01N 2015/1447; G01N 2015/1452; G01N 21/8483; G01N 15/147; G01N 15/1475; G01N 21/255; G01B 11/026; G01B 11/00; G01J 3/0278; G01P 3/68
USPC ................ 422/82.05; 73/53.01; 600/583, 319
See application file for complete search history.

(56) References Cited

U.S. PATENT DOCUMENTS 5,518,689 A  *  5/1996  Dosmann et al. .......... 422/82.05
5,701,181 A     12/1997  Boiarski et al.
(Continued)

FOREIGN PATENT DOCUMENTS

JP    2-247605 A     10/1990
JP    8-304287 A     11/1996
(Continued)

OTHER PUBLICATIONS

International Search Report (PCT/ISA/210) issued on Aug. 30, 2011, by the Japanese Patent Office as the International Searching Authority for International Application No. PCT/JP2011/066371.
(Continued)

*Primary Examiner* — Jennifer Wecker
(74) *Attorney, Agent, or Firm* — Buchanan Ingersoll & Rooney PC

(57) ABSTRACT

A component measurement device, namely a blood-glucose measurement device, that has a measurement unit that focuses measurement light on a test paper through an illumination lens and receives reflected light from the test paper. The blood-glucose measurement device measures blood components on the basis of results from detecting the reflected light. The illumination lens is provided in the measurement unit such that the focal point of the measurement light is beyond the test paper.

16 Claims, 14 Drawing Sheets

(51) Int. Cl.
   *G01N 21/55* (2014.01)
   *G01N 21/84* (2006.01)
   *G01N 15/00* (2006.01)
   *G01N 21/64* (2006.01)
   *G01N 15/14* (2006.01)
   *G01N 21/03* (2006.01)
   *G01N 21/31* (2006.01)

(52) U.S. Cl.
   CPC ...... *B65H2553/414* (2013.01); *G01N 15/1434* (2013.01); *G01N 21/0303* (2013.01); *G01N 21/31* (2013.01); *G01N 21/6456* (2013.01); *G01N 21/6486* (2013.01)

(56) References Cited

U.S. PATENT DOCUMENTS

| | | | |
|---|---|---|---|
| 2003/0142290 A1* | 7/2003 | Yamaguchi et al. | 356/28 |
| 2005/0036914 A1* | 2/2005 | Yamauchi | 422/82.05 |
| 2005/0036915 A1* | 2/2005 | Yamauchi | 422/82.05 |
| 2005/0270530 A1* | 12/2005 | Wada et al. | 356/364 |
| 2006/0040379 A1* | 2/2006 | Tanaami | 435/287.2 |
| 2006/0243031 A1* | 11/2006 | Kondo et al. | 73/53.01 |
| 2008/0049227 A1* | 2/2008 | Sacherer | 356/445 |

FOREIGN PATENT DOCUMENTS

| | | |
|---|---|---|
| JP | 9-145614 A | 6/1997 |
| JP | 2006-58044 A | 3/2006 |
| JP | 3155843 U | 12/2009 |
| WO | WO 2010/140407 A1 | 12/2010 |
| WO | WO 2010140407 A1 * | 12/2010 |

OTHER PUBLICATIONS

Written Opinion (PCT/ISA/237) issued on Aug. 30, 2011, by the Japanese Patent Office as the International Searching Authority for International Application No. PCT/JP2011/066371.

* cited by examiner

COMPONENT MEASUREMENT DEVICE

TECHNICAL FIELD

The present invention relates to a component measuring device for optically measuring a biological component in a body fluid.

BACKGROUND ART

Heretofore, component measuring devices have been used to detect a biological component contained in a body fluid such as blood or urine and optically measure the amount and properties of the detected biological component. For example, Japanese Laid-Open Patent Publication No. 09-145614 discloses a diffused light reflection reading pad as a device for detecting glucose in blood. Specifically, when a reagent test pad that has been colored by blood is irradiated with light (irradiation light) from an irradiating means, the reagent test pad reflects the light, which is applied to a light sensor to detect glucose in the blood.

SUMMARY OF INVENTION

Component measuring devices which incorporate the above optical system normally have an aperture or opening for adjusting the area irradiated with the irradiating light and the amount of the irradiating light. For example, the diffused light reflection reading head disclosed in Japanese Laid-Open Patent Publication No. 09-145614 has an irradiating port that passes an LED light therethrough. The irradiating port functions as an aperture for shaping the light into a spot having a suitable size (area) and intensity (amount of light).

Although not disclosed in Japanese Laid-Open Patent Publication No. 09-145614, there is a component measuring device having a lens for focusing irradiation light onto an object to be measured, i.e., a target object. Such a component measuring device also needs to have an aperture for adjusting the shape of a spot of irradiation light and reducing stray light. Specifically, the aperture is disposed on the path of the irradiation light to regulate the degree to which the irradiation light is limited, i.e., the area of the spot and the amount of irradiation light, for thereby focusing the irradiation light in front of the target object.

However, the aperture included in the component measuring device is disadvantageous in that the number of parts used increases or parts used tend to be complex in shape. As a result, the number of steps of manufacturing the parts increases and the process of assembling the parts is complicated, resulting in an increase in the cost paid to manufacture the component measuring device. Another problem is that since the amount of light is reduced by the aperture, the sensitivity of biological component measurement is lowered.

According to the component measuring device wherein the lens focuses the irradiation light, especially, in front of the target object, when the distance and angle between the lens and the target object vary due to wobbling of the component measuring device and a positional error of the target object, the amount of irradiation light that is applied to the target object also varies, causing the accuracy of the component measurement to vary.

The present invention has been made in view of the above drawbacks. It is an object of the present invention to provide a component measuring device of simple constitution which is capable of applying a desired amount of irradiation light to a target object in a predetermined range thereon, increasing the accuracy of component measurement, and reducing the cost paid to manufacture itself by reducing the number of parts used.

To achieve the above object, there is provided in accordance with the present invention a component measuring device including a measuring unit for applying measuring irradiation light through an irradiation light lens to an object to be measured and detecting reflected light from the object, a component in a liquid absorbed by the object being measured based on the detected reflected light, wherein the irradiation light lens is included in the measuring unit such that a focal position of the irradiation light is farther than a disposed position of the object.

Since the focal point of the irradiation light is placed at the position which is farther than the object, when the component measuring device wobbles or the object is positioned with an error, changing the angle or the distance from the irradiation light lens to the object, the amount of irradiation light changes more gradually than if the focal point is closer than the object. Therefore, a stable amount of irradiation light is applied within a predetermined measuring range on the object for a stabler accuracy of component measurement.

The measuring unit may comprise a light emitter for emitting the irradiation light, and a photometric block having an irradiation light path for disposing the light emitter so as to face the irradiation light lens, the irradiation light path extending from a disposed position of the light emitter to a disposed position of the irradiation light lens.

Since the light emitter and the irradiation light lens are disposed so as to face each other, the irradiation light emitted from the light emitter is guided through the irradiation light path to the lens.

The distance from the light emitter to the irradiation light lens may be substantially equal to a distance from the irradiation light lens to the object. As the distance from the light emitter to the lens is substantially equal to the distance from the lens to the object, the worker can easily grasp shape errors and assembled states of various components, and adjust the two distances appropriately for thereby reducing variations which may occur when individual component measuring devices are assembled. Any adverse effects of shape errors and assembling errors of the components can be minimized by arranging the light emitter, the irradiation light lens, and the object at substantially equal intervals. Specifically, if the irradiation light lens is positioned more closely to the light emitter or the object, then any layout errors tend to adversely affect a measuring process. However, the light emitter, the irradiation light lens, and the object that are arranged at substantially equal intervals make it possible to reduce adverse effects on the measuring process.

The irradiation light path of the photometric block may include stray light guiding means for guiding stray light reflected by an inner peripheral surface of the irradiation light path out of a measuring range on the object through the irradiation light lens.

Since the stray light guiding means thus provided is able to guide stray light reflected by the inner peripheral surface of the irradiation light path out of the measuring range on the object, the stray light that is included in the reflected light detected by the measuring unit is reduced. The measuring unit is thus capable of detecting a stable amount of reflected light that does not include stray light for accurately measuring a component on the object.

The inner peripheral surface of the irradiation light path may be of a hollow cylindrical shape, and the stray light guiding means may be of a female screw configuration. The female screw configuration can be formed on the inner peripheral surface of the irradiation light path by a male screw molding member when the photometric block is molded. Therefore, the photometric block can easily be molded as it is not necessary to carry out a troublesome process such as a process of producing a complex mold for molding the photometric block.

The inner peripheral surface of the irradiation light path may be of a tapered shape that is progressively smaller in diameter toward the irradiation light lens. Accordingly, when the inner peripheral surface of the irradiation light path is of a tapered shape, after the irradiation light path is molded into the female screw configuration, it can easily be removed from the mold simply by turning the male screw molding member. As a result, the process of molding the photometric block can efficiently be performed.

The stray light guiding means should preferably comprise an alternately successive array of a ridge and a recess on the inner peripheral surface of the irradiation light path, and an angle of the surface of the ridge which faces the light emitter should preferably be set to prevent the stray light from being applied to the irradiation light lens. As the angle of the surface of the ridge which faces the light emitter with respect to the inner peripheral surface of the irradiation light path is set to prevent the stray light from being applied to the irradiation light lens, the stray light that is reflected by the irradiation light path is not focused by the irradiation light lens. Consequently, the stray light is prevented reliably from being included in the reflected light that is detected by the measuring unit.

The measuring unit may comprise a plurality of the light emitters disposed so as to face the irradiation light lens. Since the single irradiation light lens is provided with respect to the plural light emitters, the irradiation light lens may have a larger planar area in the measuring unit than if a plurality of irradiation light lenses are associated with the respective light emitters. The irradiation light lens is thus capable of collecting an increased amount of irradiation light and focusing it onto the object for a higher accuracy of component measurement.

The measuring unit may comprise a light detector for detecting the reflected light, and the irradiation light lens may be integrally formed with a reflected light lens for focusing the reflected light onto the light detector. As the irradiation light lens and the reflected light lens are integrally formed with each other, a process of positioning them is dispensed with at the time they are assembled, and the component measuring device is made up of a reduced number of parts and can be manufactured at a reduced cost.

The photometric block should preferably include a reflected light path extending from a disposed position of the reflected light lens to a disposed position of the light detector. Since a separate reflected light path does not need to be added, the manufacturing cost of the component measuring device is reduced.

According to the present invention, a desired amount of irradiation light can be applied within a predetermined range on the object to be measured for an increased accuracy of component measurement, and the component measuring device is made up of a reduced number of parts and can be manufactured at a significantly reduced cost.

DESCRIPTION OF EMBODIMENTS

A component measuring device according to a preferred embodiment of the present invention will be described in detail below with reference to the accompanying drawings.

According to the embodiment, a blood sugar level measuring device for measuring mainly a blood sugar level among a plurality of blood components will be described in detail as the component measuring device. The blood sugar level measuring device is a device used by the doctor, nurse, or diabetic patient to take a blood sample, measure a blood sugar level of the blood sample, and manage the data of the measured blood sugar level. The component measuring device is not limited to a blood sugar level measuring device.

Figure 1:
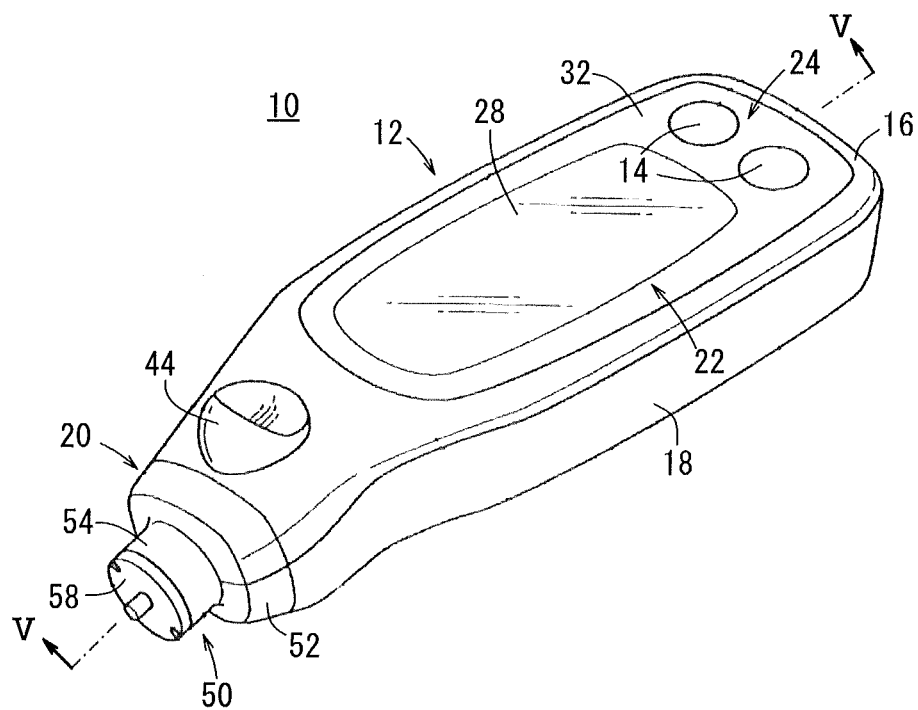
FIG. 1 is a perspective view of a general makeup of a blood sugar level measuring device according to an embodiment of the present invention.
Figure 2:
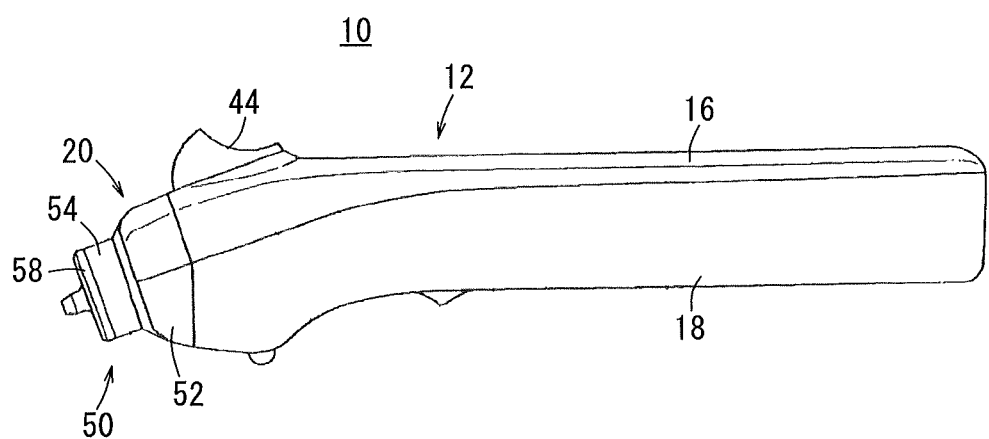
FIG. 2 is a side view of the blood sugar level measuring device shown in FIG. 1.
Figure 3:
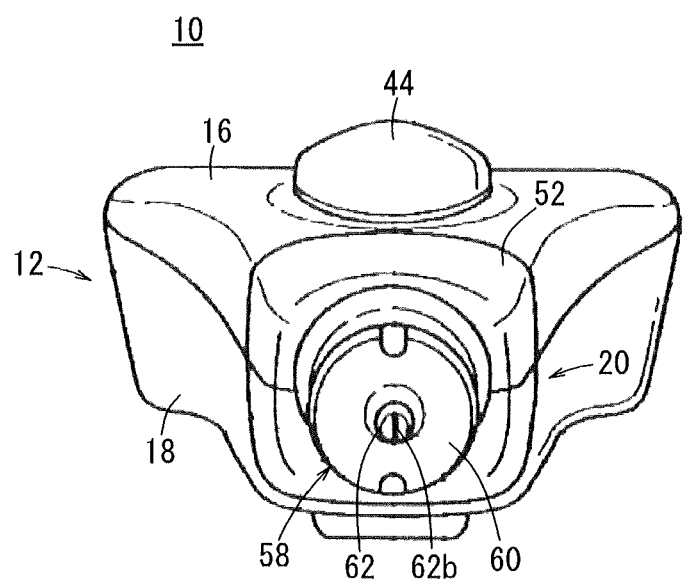
FIG. 3 is a front view of the blood sugar level measuring device shown in FIG. 1.
Figure 4:
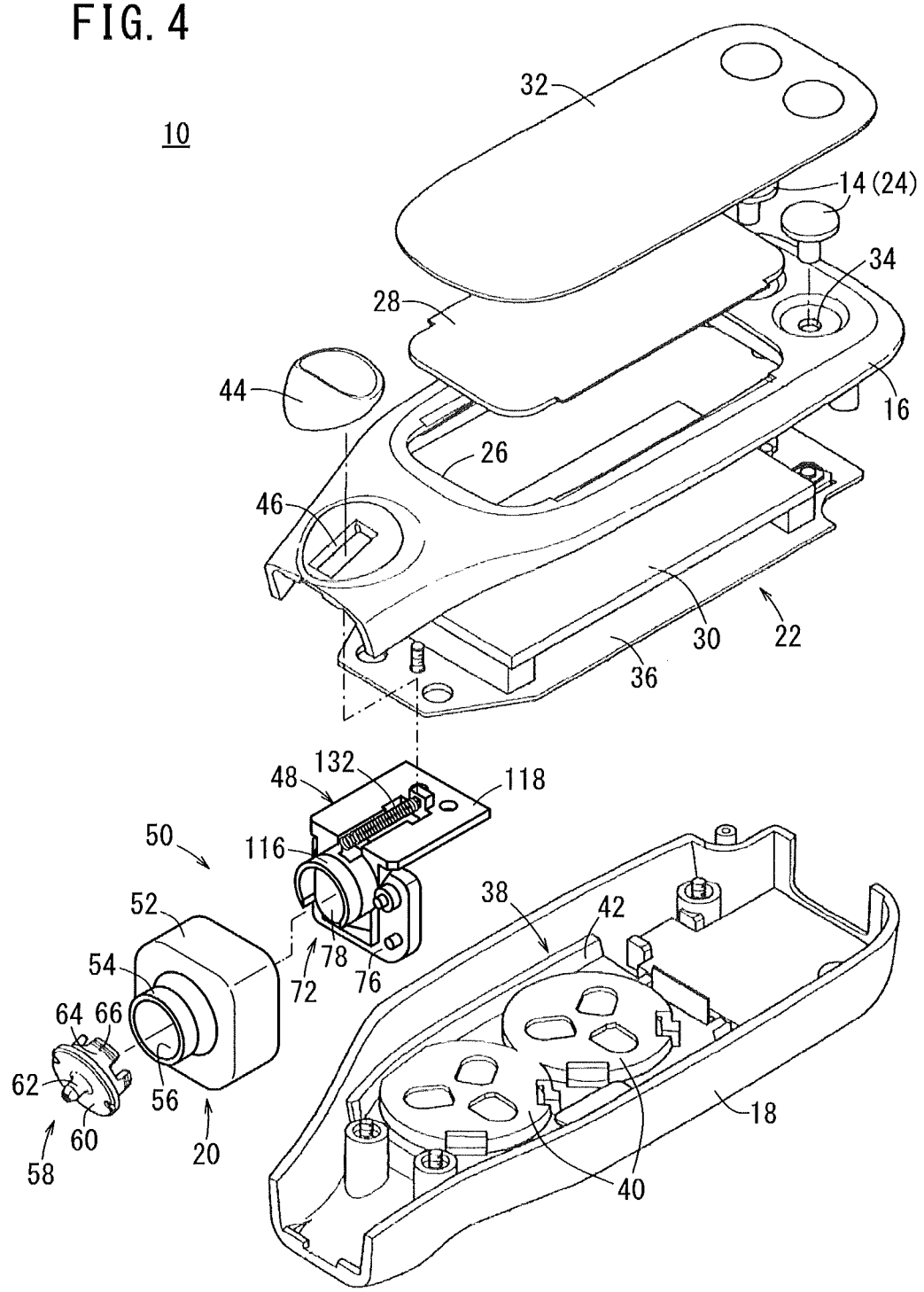
FIG. 4 is an exploded perspective view of the blood sugar level measuring device shown in FIG. 1.
Figure 5:
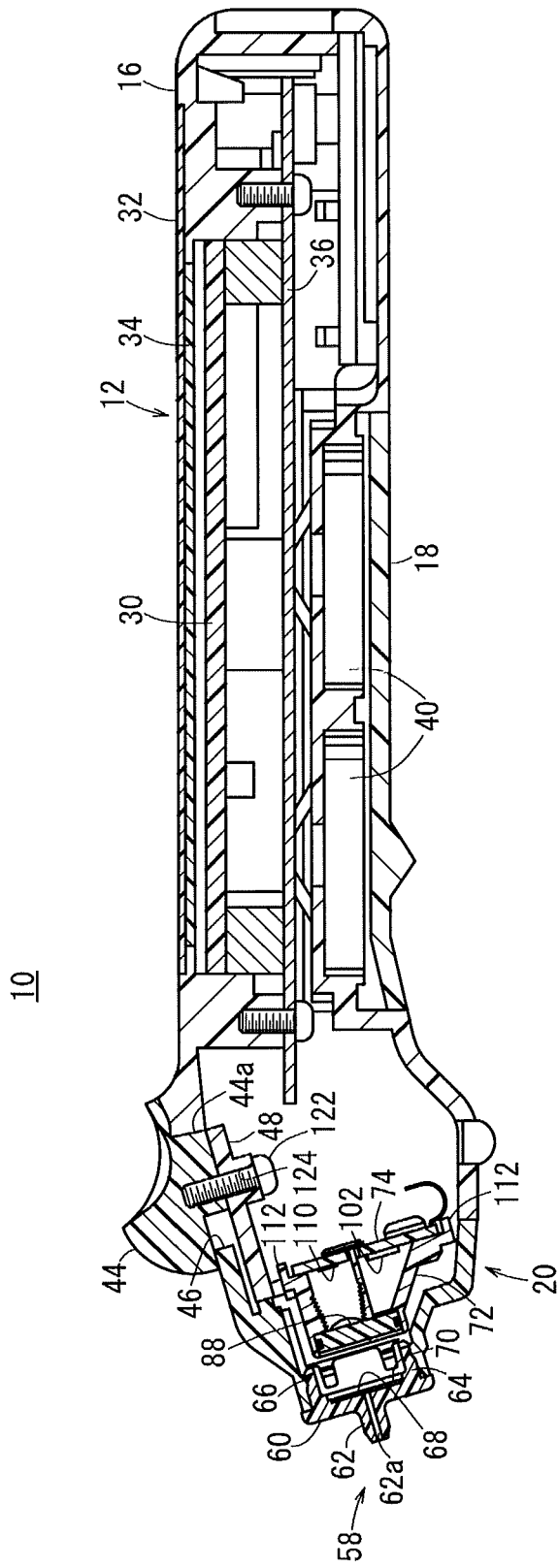
FIG. 5 is a cross-sectional view of the blood sugar level measuring device taken along line V-V of FIG. 1.

FIG. 1 is a perspective view of a general makeup of a blood sugar level measuring device, i.e., a component measuring device, according to the embodiment. FIG. 2 is a side view of the blood sugar level measuring device. FIG. 3 is a front view of the blood sugar level measuring device. FIG. 4 is an exploded perspective view of the blood sugar level measuring device. FIG. 5 is a cross-sectional view taken along line V-V of FIG. 1.

As shown in FIGS. 1 through 3, a blood sugar level measuring device 10 has a casing 12 that provides a basis for the appearance of the blood sugar level measuring device 10. The casing 12 is of a three-dimensional shape which is somewhat slender and fits with a hand so that the user can hold it with one hand and can easily press operating switches 14. The casing 12 includes an upper case 16, a lower case 18, and a distal case 20. The casing 12 is assembled by placing the upper case 16 on the lower case 18 vertically and mounting the distal case 20 on the distal end portions of the upper case 16 and the lower case 18. The casing 12 has a display unit 22 for displaying items of information to be entered and confirmed for measuring a blood sugar level and also displaying a measured result, etc., and an operating section 24 including two operating switches 14.

As shown in FIG. 4, the display unit 22 of the blood sugar level measuring device 10 has a liquid crystal cover 28 fitted in a window 26 formed in the upper case 16 and a liquid crystal panel 30 disposed in a lower layer of the liquid crystal cover 28. A front panel 32, which is of a size large enough to cover the liquid crystal cover 28 and the two operating switches 14, is applied to an upper surface of the upper case 16.

The two operating switches 14 are inserted in respective insertion holes that are formed in upper surface of the upper case 16. The operating section 24 allows various actions such as the turning on and off of the blood sugar level measuring device 10 to be made through the operating switches 14.

The liquid crystal panel 30 of the display unit 22 and a main wiring board 36 for controlling the blood sugar level measuring device 10 are disposed on the reverse side of the upper case 16, i.e., within the casing 12, which incorporates the display unit 22 and the operating section 24. The main wiring board 36 has an electric circuit of a predetermined shape made up of printed interconnects, etc. The main wiring board 36 supports thereon a microcomputer for executing preset processes, storage devices such as a ROM and a RAM storing preset programs, and electronic parts including capacitors, resistors, etc. (not shown).

A cell storage unit 38 is disposed on an upper surface of the lower case 18, i.e., within the casing 12. The cell storage unit 38 stores therein button cells 40 as a portable power supply. The cell storage unit 38 is openably covered with a cell cover 42 that is removably mounted on the lower case 18. The main wiring board 36 is controlled and the display unit 22 is energized to display information by electric power supplied from the button cells 40 in the blood sugar level measuring device 10. The power supply used in the blood sugar level measuring device 10 is not limited to button cells, but may comprise circular cells, rectangular cells, secondary cells, or an external power supply connected by a power cord.

As shown in FIGS. 1 and 2, the casing 12, which includes the upper case 16 and the lower case 18 stacked together, is tapered from an intermediate portion thereof toward its distal end portion, and is curved toward the lower case 18. The distal case 20 is mounted on the distal end portion of the casing 12 for use as a casing of a measuring unit 50 which detects blood.

The upper case 16 has a slot 46 formed in its upper surface near the distal end portion (see FIG. 4). The slot 46 serves to guide an ejector slider 44 to move therealong. The slot 46 extends linearly over a predetermined distance in the longitudinal directions of the casing 12. The ejector slider 44 has a leg 44a slidably inserted in the slot 46 (see FIG. 5). An ejector 48 is screwed to the leg 44a within the casing 12. The ejector slider 44 is able to push the ejector 48 for sliding movement.

As shown in FIG. 4, the distal case 20 has a square tube 52 attached to the upper case 16 and the lower case 18 and a circular tube 54 disposed on a distal end side of the square tube 52. The square tube 52 houses therein various components for optically measuring blood. The circular tube 54 has an opening 56 formed in its distal end face, and a measuring tip 58 is detachably mounted in the opening 56.

The measuring tip 58 has a base 60 in the shape of a disc, a nozzle 62 disposed on a distal end face of the base 60, and an engaging portion 64 disposed on the base 60 remotely from the nozzle 62. The base 60 has a diameter substantially equal to the outside diameter of the circular tube 54. The nozzle 62 projects centrally from the base 60. The nozzle 62 has a sampling hole 62a formed therein along a central axis thereof and extending from its distal end face to the rear surface of the base 60 (see FIG. 5). The nozzle 62 has a groove 62b formed in its distal end face for making it easy for the nozzle 62 to draw in blood (see FIG. 3).

The engaging portion 64 of the measuring tip 58 is of a hollow cylindrical shape and has an outside diameter such that the engaging portion 64 fits in the opening 56 of the circular tube 54. The engaging portion 64 has four resilient locking pieces (locking portions) 66 projecting rearwardly therefrom. The locking pieces 66 have respective protrusions 66a on outer circumferential surfaces thereof for engaging a ridge 54a in the circular tube 54 when the locking pieces 66 are inserted in the circular tube 54. When the protrusions 66a move over the ridge 54a and then are locked by the ridge 54a, the measuring tip 58 is mounted in the circular tube 54 (see FIG. 8).

As shown in FIG. 5, the engaging portion 64 has a test paper housing region 68 held in fluid communication with the sampling hole 62a. The test paper housing region 68 houses therein a test paper (object to be measured) 70 which will be impregnated with blood when a blood sample is taken. The blood sugar level measuring device 10 applies irradiation light to the test paper 70 and detects reflected light from the test paper 70 to measure a blood component.

Figure 6:
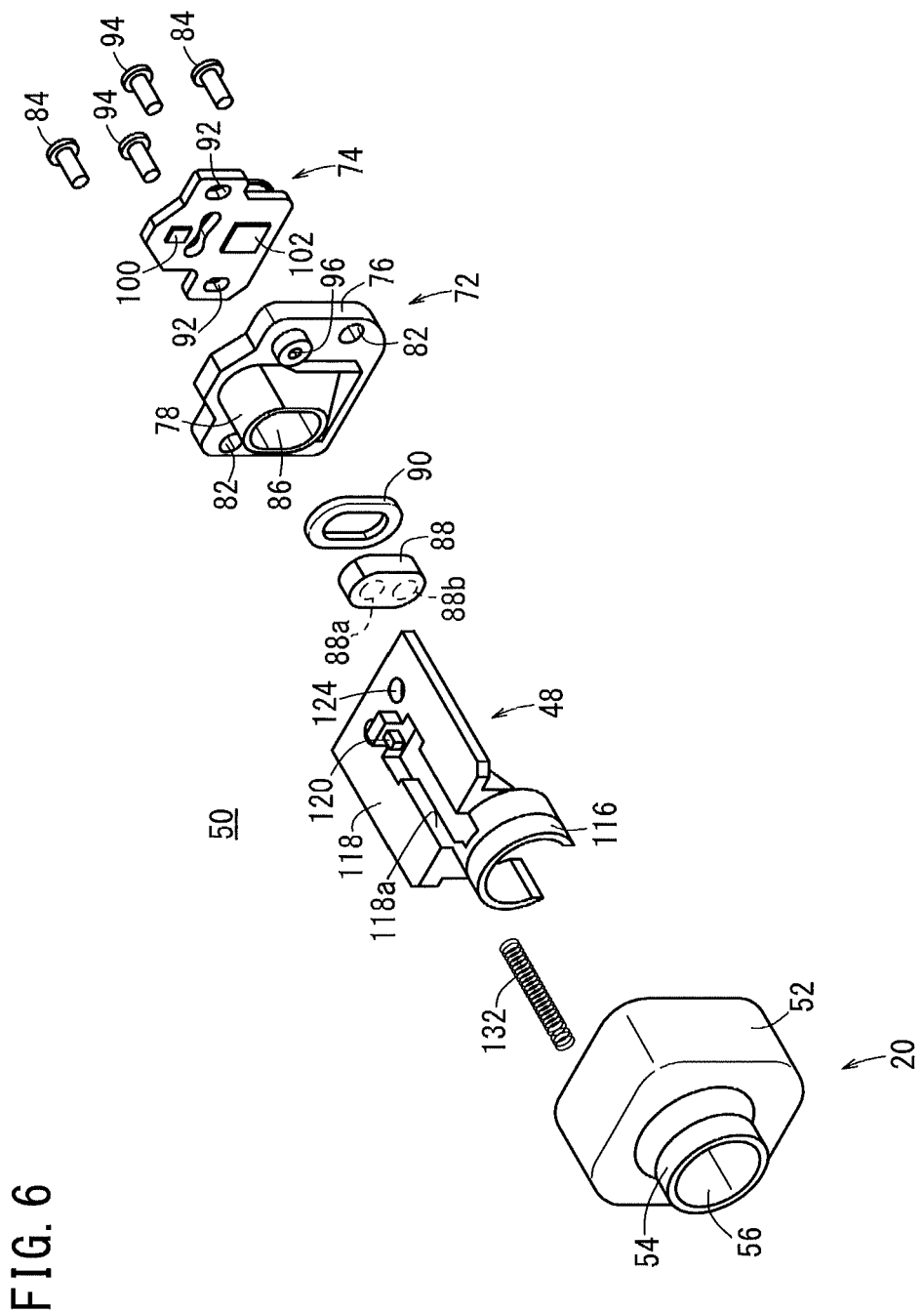
FIG. 6 is an exploded perspective view of a measuring unit of the blood sugar level measuring device according to the embodiment of the present invention.
Figure 7:
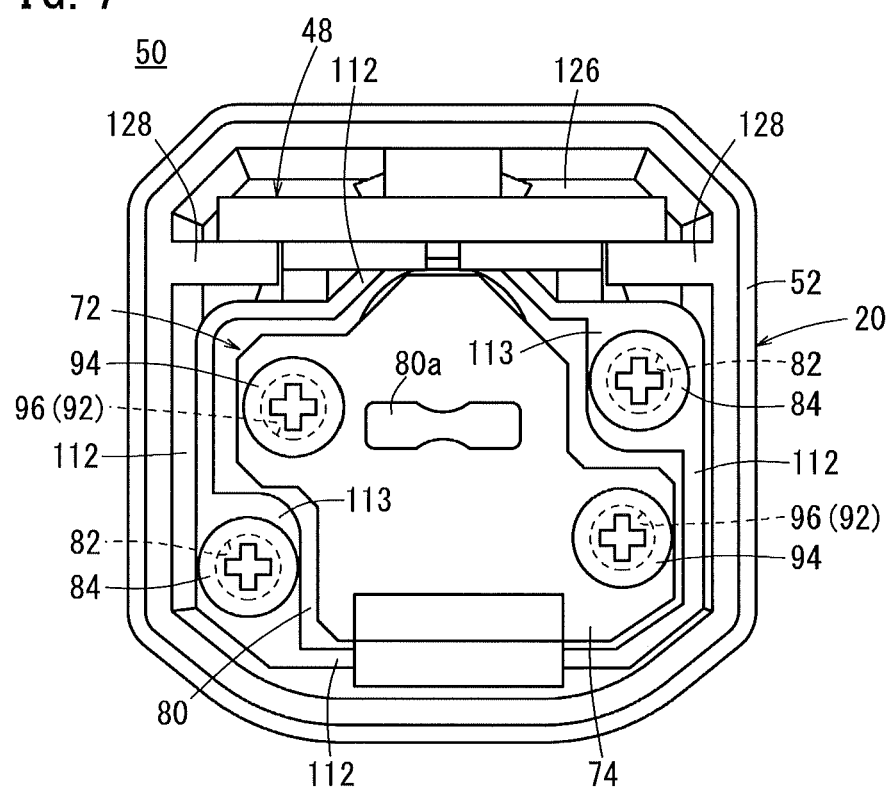
FIG. 7 is a rear view of the blood sugar level measuring device shown in FIG. 5.
Figure 8:
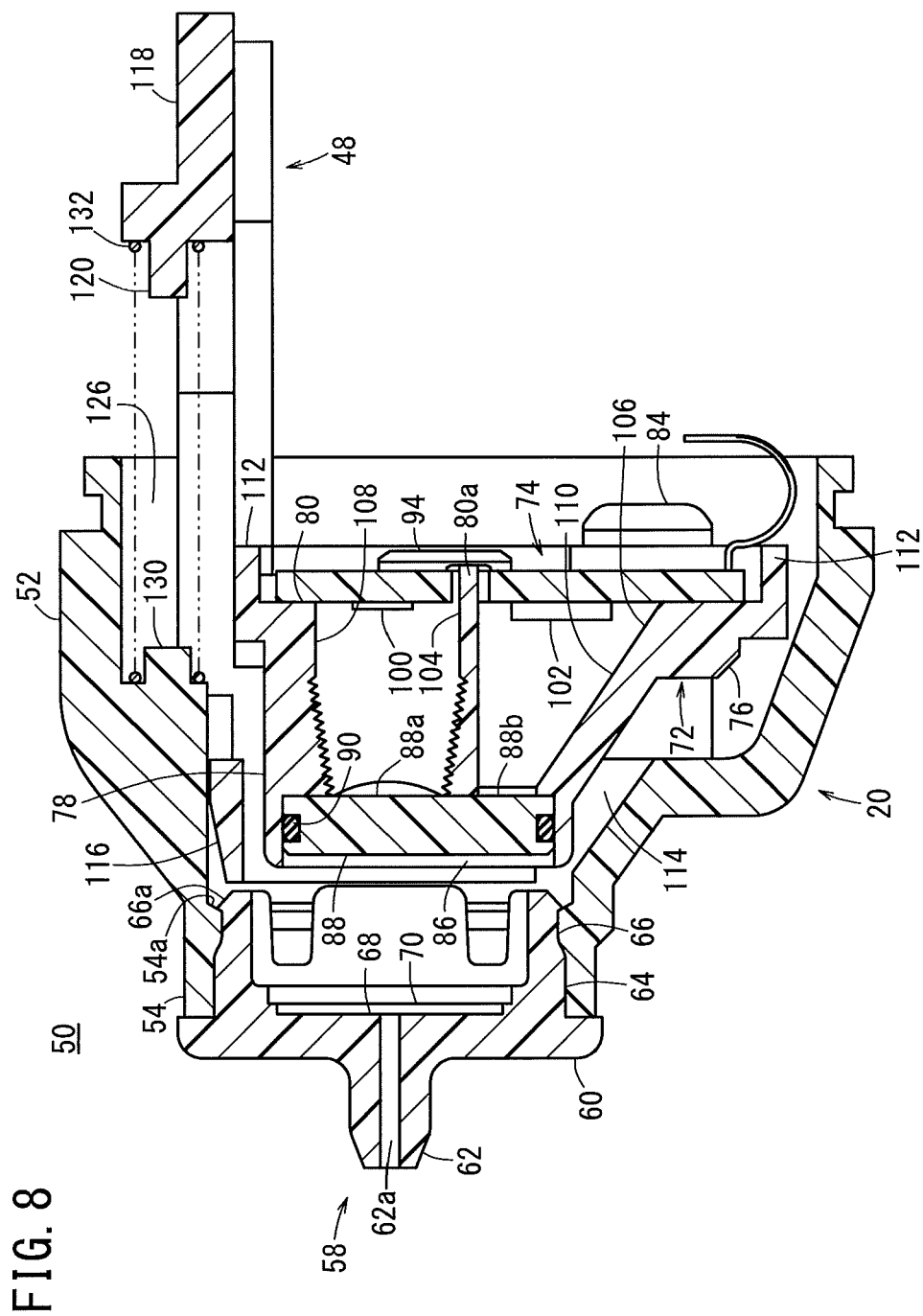
FIG. 8 is a sectional side view of the blood sugar level measuring device shown in FIG. 5.
Figure 9:
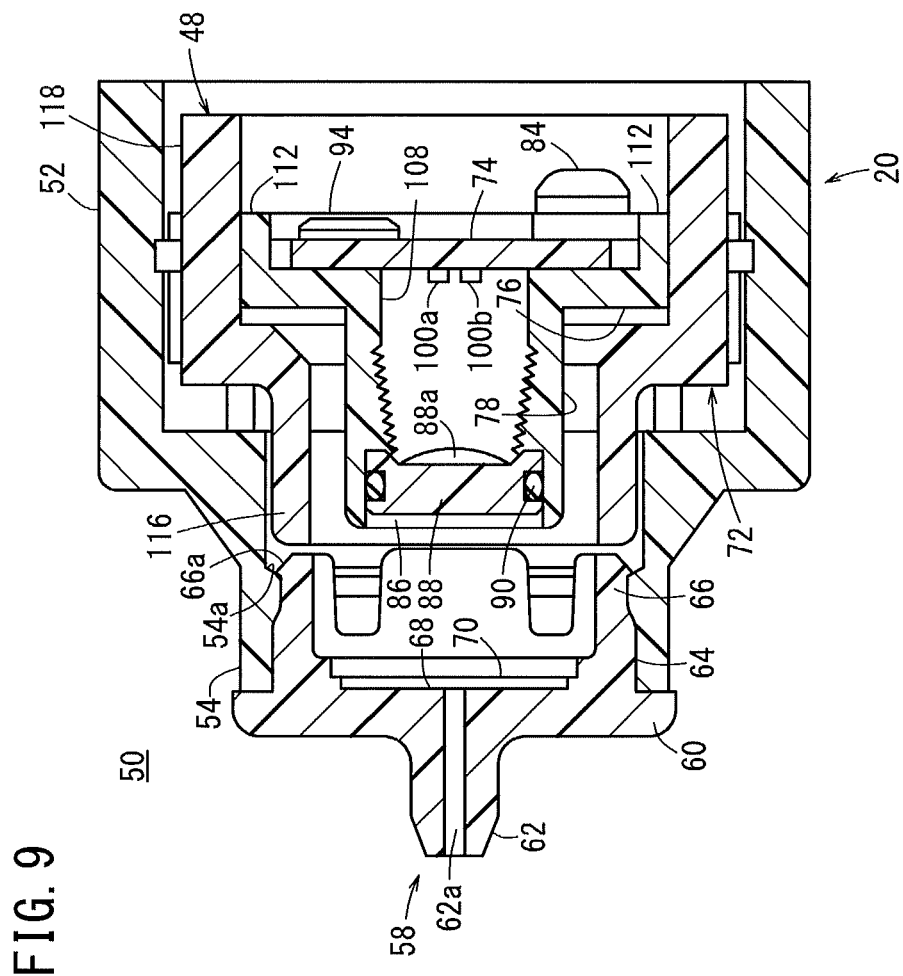
FIG. 9 is a sectional plan view of the blood sugar level measuring device shown in FIG. 5.

FIG. 6 is an exploded perspective view of the measuring unit 50 of the blood sugar level measuring device 10 according to the present embodiment. FIG. 7 is a rear view of the measuring unit 50. FIG. 8 is a sectional side view of the measuring unit 50. FIG. 9 is a sectional plan view of the measuring unit 50.

The measuring unit 50 of the blood sugar level measuring device 10 is an assembly for optically measuring a blood component sampled by the measuring tip 58. As shown in FIG. 6, the measuring unit 50 includes the distal case 20, a photometric block 72, a board 74, and the ejector 48. As described above, the distal case 20 includes the square tube 52 and the circular tube 54, and is mounted on the distal end portion of the casing 12 which is made up of the upper case 16 and the lower case 18 stacked together. The distal case 20 is molded of synthetic resin such as ABS resin, polycarbonate, or the like.

The photometric block 72 is a member which holds the board 74 that detects a blood component and which is mounted in the distal case 20. The photometric block 72, which may be molded of the same material as the distal case 20, has a proximal end portion 76 in the form of a flat plate and a protrusion 78 projecting from the proximal end portion 76 to the distal end of the measuring unit 50.

As shown in FIG. 8, the protrusion 78 is disposed on the front surface of the proximal end portion 76 of the photometric block 72. The proximal end portion 76 has a board placement region 80 on its rear surface. The board placement region 80 is of a flat shape for placing the board 74 thereon. A positioning projection 80a for positioning the board 74 is disposed substantially centrally in the board placement region 80. The positioning projection 80a extends through the board 74 and is interposed between light emitters 100 and a light detector 102, to be described later, for preventing light from being propagated directly from the light emitters 100 to the light detector 102.

The proximal end portion 76 has two mounting screw holes 82 formed therein (see FIG. 7). Mounting screws 84 are inserted from behind the photometric block 72 into the respective mounting screw holes 82, and screwed into female screw holes, not shown, formed in the distal case 20, thereby fastening the photometric block 72 to the distal case 20.

As shown in FIG. 6, the protrusion 78 of the photometric block 72 is in the shape of an oblong hollow cylinder having straight side surfaces and arcuate upper and lower surfaces. The protrusion 78 has a protrusion opening 86 formed in a front surface thereof. A lens assembly 88 is mounted in the protrusion opening 86. The lens assembly 88 attached to the photometric block 72 includes an upper irradiation light lens 88a and a lower reflected light lens 88b that are integrally formed with each other. The lens assembly 88, with an O-ring 90 fitted in a circumferential side wall thereof, is mounted in the protrusion opening 86, so that the protrusion opening 86 is hermetically sealed by the lens assembly 88.

The board 74 of the measuring unit 50 has a shape for being placed on the board placement region 80. The board 74 has two board-side screw holes 92 at predetermined portions. From behind the board 74, board-mounting screws 94 are inserted into the respective board-side screw holes 92, and screwed into board-securing holes 96 formed in the board placement region 80, thereby providing the board 74 on the photometric block 72.

The board 74 supports on its surface facing the board placement region 80 the two light emitters 100 for emitting irradiation light (a first light emitter 100a and a second light emitter 100b, see FIG. 9), the light detector 102 for detecting reflected light, and various electronic components required to detect a blood component. The light emitters 100 may comprise a light-emitting diode (LED) for emitting light having a predetermined wavelength, for example, and the light detector may comprise a photodiode (PD), for example. According to the present embodiment, the light emitters 100 and the light detector 102 that are mounted on the board 74 are free of a shell-shaped shield (transmissive body) to make the board 74 and the blood sugar level measuring device 10 small in size.

As shown in FIG. 8, when the board 74 is to be placed on the board placement region 80 of the photometric block 72, the light emitters 100 and the light detector 102 are positioned so as to face the board placement region 80. The board placement region 80 has two openings, i.e., an irradiation light board-side opening 104 and a reflected light board-side opening 106 formed therein. When the board 74 is placed on the board placement region 80, the light emitters 100 are disposed in the irradiation light board-side opening 104 and the light detector 102 is disposed in the reflected light board-side opening 106.

The irradiation light board-side opening 104 communicates with an irradiation light path 108 and the reflected light board-side opening 106 communicates with a reflected light path 110. The irradiation light path 108 and the reflected light path 110 extend through the proximal end portion 76 and the protrusion 78, and are held in communication with the protrusion opening 86 on the distal end side thereof. Since the irradiation light path 108 and the reflected light path 110 are formed in the photometric block 72, the blood sugar level measuring device 10 is made up of a reduced number of parts and can be manufactured at a reduced cost.

With the board 74 placed on the board placement region 80, the light emitters 100 are disposed on a proximal end side of the irradiation light path 108. Irradiation light emitted from the light emitters 100 are guided through the irradiation light path 108 to the lens assembly 88 and applied through the lens assembly 88 to the test paper 70. The light detector 102 is on a proximal end side of the reflected light path 110. Reflected light from the test paper 70 is guided through the lens assembly 88 and the reflected light path 110 and then detected by the light detector 102.

According to the present embodiment, the proximal end portion 76 of the photometric block 72 has a partition 112 on its rear surface which projects rearwardly from the board placement region 80. With the board 74 placed on the board placement region 80, the partition 112 surrounds all the sides of the rear surface of the photometric block 72, and projects rearwardly beyond the board 74, thereby preventing a liquid from contacting the board 74 and also preventing dust, etc. from adhering to the board 74.

With the photometric block 72 mounted in the distal case 20, a clearance 114 is formed between the inner peripheral surface of the distal case 20 and the side surfaces of the protrusion 78 of the photometric block 72. The ejector 48 is slidably disposed in the clearance 114.

As shown in FIG. 6, the ejector 48 of the measuring unit 50 include a pusher 116 on its distal end side and a slide plate 118 to which the pusher 116 is fixed, the slide plate 118 being slidable a predetermined distance. The pusher 116 is of an arcuate shape formed by cutting a certain length off a lower portion of a hollow cylindrical shape.

The slide plate 118 is in the shape of a flat plate extending rearwardly from the pusher 116. The slide plate 118 has a slot 118a longitudinally formed centrally therein and a projection 120 for a spring at the rear end of the slot 118a. The slide plate 118 also has an ejector screw hole 124 formed in a rear portion thereof. The leg 44a of the ejector slider 44 is engagingly fastened to the slide plate 118 by an ejector screw 122 inserted in the ejector screw hole 124 (see FIG. 5).

As shown in FIG. 7, the distal case 20 has an ejector placement region 126 that houses therein a distal end side of the ejector 48. The ejector placement region 126 is formed in an upper portion of the square tube 52 by support pieces 128 which support opposite side ends of the slide plate 118 and a projection 130 for a spring (see FIG. 8) projecting rearwardly from an upper central portion of the square tube 52.

As shown in FIGS. 6 and 8, the ejector 48 is placed in the ejector placement region 126 with a spring 132 disposed in the slot 118a. The projection 120 for a spring is inserted in an end of the spring 132 and the projection 130 for a spring is inserted in the other end of the spring 132.

While the photometric block 72 and the ejector 48 are placed in the distal case 20, the pusher 116 is disposed on the outer peripheral surface, i.e., the upper surface and the both side surfaces, of the protrusion 78 of the photometric block 72. The ejector 48 is slidable toward the distal and rear ends of the casing 12. When the ejector 48 slides, the pusher 116 moves in one direction or the other on the outer peripheral surface of the protrusion 78, i.e. in the clearance 114. While the measuring tip 58 is mounted on the distal case 20, the movement of the ejector 48 toward the distal end of the casing 12 causes the pusher 116 to push the locking pieces 66 of the measuring tip 58 until the measuring tip 58 is removed from the casing 12.

A process of measuring a blood component using the blood sugar level measuring device 10 according to the present embodiment will be described below. For measuring a blood component, the blood of the user is sampled using the casing 12 with the measuring tip 58 mounted thereon. Specifically, a fingertip of the user is punctured by a dedicated puncturing device, not shown, allowing a small amount of blood, e.g., in the range from 0.3 to 1.5 μL, to flow onto the skin. Then, the distal end of the nozzle 62 of the measuring tip 58 that is mounted on the distal end of the blood sugar level measuring device 10 is brought into contact with the blood from the fingertip.

The blood flows through the groove 62b in the distal end of the nozzle 62 into the sampling hole 62a, and is attracted to the rear end of the sampling hole 62a by a capillary action. Then the test paper 70 housed in the test paper housing region 68 is impregnated with the blood, and the blood spreads radially-outwardly in the test paper 70 in a circular pattern. At the same time that the blood thus spreads, the glucose in the blood reacts with a chromogenic agent included in the test paper 70, which is then colored depending on the amount of the glucose.

Figure 10:
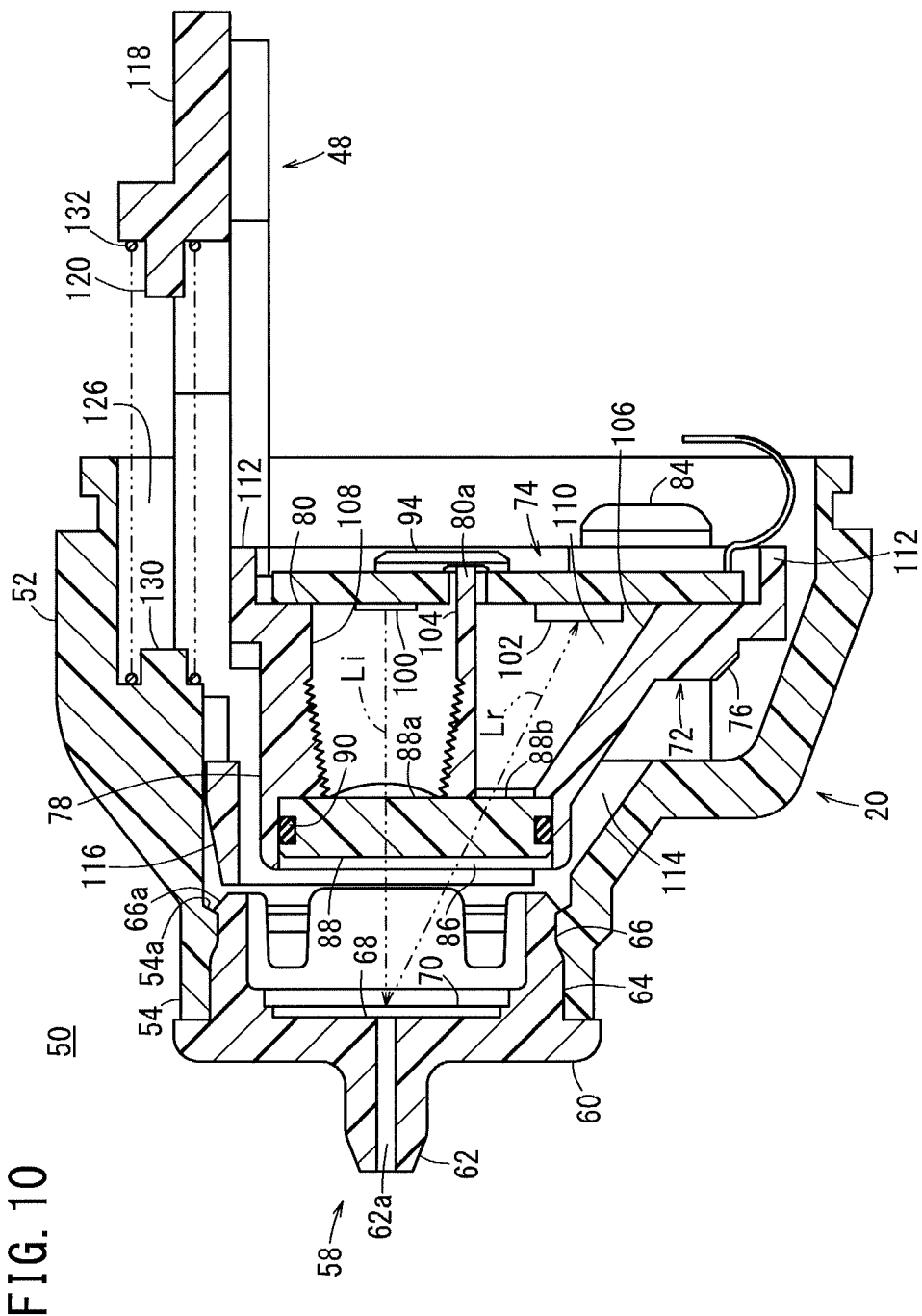
FIG. 10 is a view showing the manner in which a blood component is actually detected by the blood sugar level measuring device according to the embodiment.

FIG. 10 is a view showing the manner in which a blood component is actually detected by the blood sugar level measuring device 10 according to the embodiment. As shown in FIG. 10, the first light emitter 100a or the second light emitter 100b emits irradiation light Li, which passes through the irradiation light path 108 to the irradiation light lens 88a. The irradiation light Li is then focused by the irradiation light lens 88a onto the test paper 70.

The irradiation light Li applied to the test paper 70 is reflected thereby and applied as reflected light Lr to the reflected light lens 88b. The reflected light Lr that is applied to the reflected light lens 88b is focused by the reflected light lens 88b and applied through the reflected light path 110 to the light detector 102, which measures the amount of the applied reflected light Lr. In this manner, the blood sugar level measuring device 10 measures the degree of the color of the test paper 70.

In order for the blood sugar level measuring device 10 to measure a blood sugar level, the first light emitter 100a and the second light emitter 100b alternately emits the irradiation light Li. The irradiation light Li that is emitted by the first light emitter 100a is used to detect a pigment produced by the reaction between the chromogenic agent and the glucose, and to measure the degree of coloring corresponding to the glucose amount. The irradiation light Li that is emitted by the second light emitter 100b is used to detect red blood cells, measuring the density of red of the red blood cells. The level of glucose that is obtained from the degree of coloring is adjusted by a hematocrit value that is obtained from the density of red of the red blood cells, and the adjusted level of glucose is quantified to determine a blood sugar level.

After the measurement, the measuring tip 58 is removed from the casing 12 as follows: The user pushes the ejector slider 44 toward the distal end side of the blood sugar level measuring device 10 to slide the ejector 48 forwardly, i.e., toward the distal end side. The pusher 116 of the ejector 48 presses the locking pieces 66 of the measuring tip 58 forwardly until the measuring tip 58 is dislodged. For measuring a blood component again, a new measuring tip 58 is mounted on the distal case 20. Since the measuring tip 58 can thus easily be replaced with a new one, a blood component can efficiently be measured.

The user can easily remove the measuring tip 58 from the blood sugar level measuring device 10 with one hand. Since the measuring tip 58 is installed on the distal end of the casing 12 that is curved toward the lower case 18, the user can simply and quickly discard the measuring tip 58 by moving the ejector slider 44 without touching the measuring tip 58.

Figure 11A:
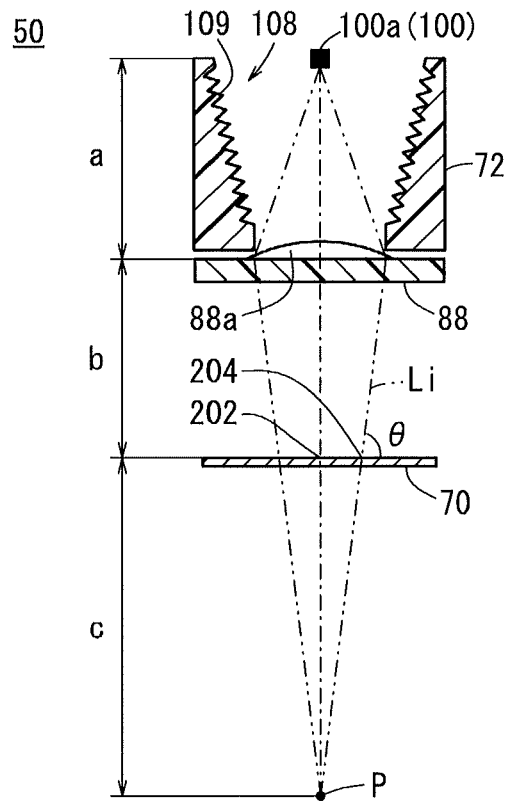
FIGS. 11A and 11B are views schematically showing the manner in which measuring units apply irradiation light, FIG. 11A showing the manner in which the measuring unit according to the embodiment applies irradiation light and FIG. 11B showing the manner in which a conventional measuring unit with an aperture applies irradiation light.
Figure 11B:
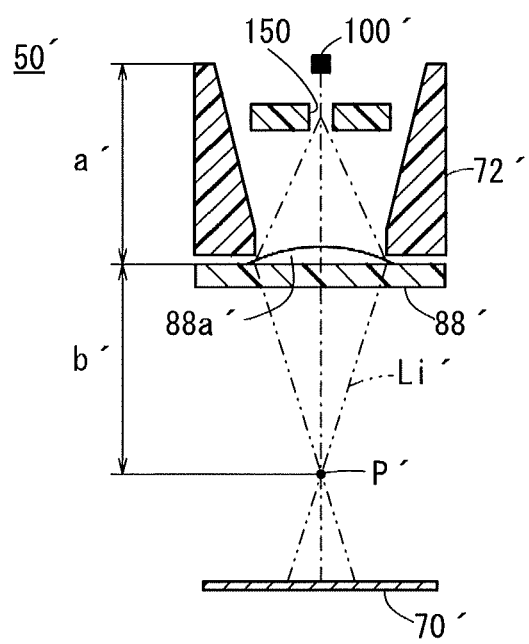
Figure 12A:
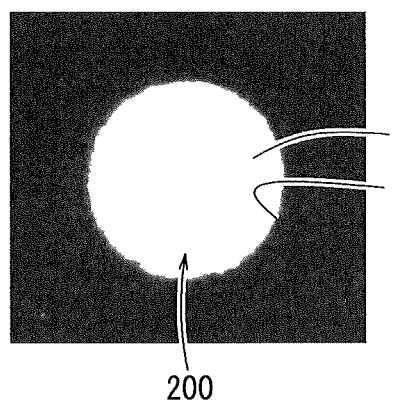
FIG. 12A is a view showing the manner in which the irradiation light shown in FIG. 11A is applied.
Figure 12B:
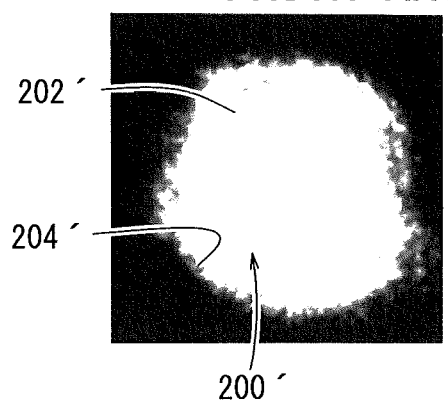
FIG. 12B is a view showing the manner in which the irradiation light shown in FIG. 11B is applied.
Figure 12C:
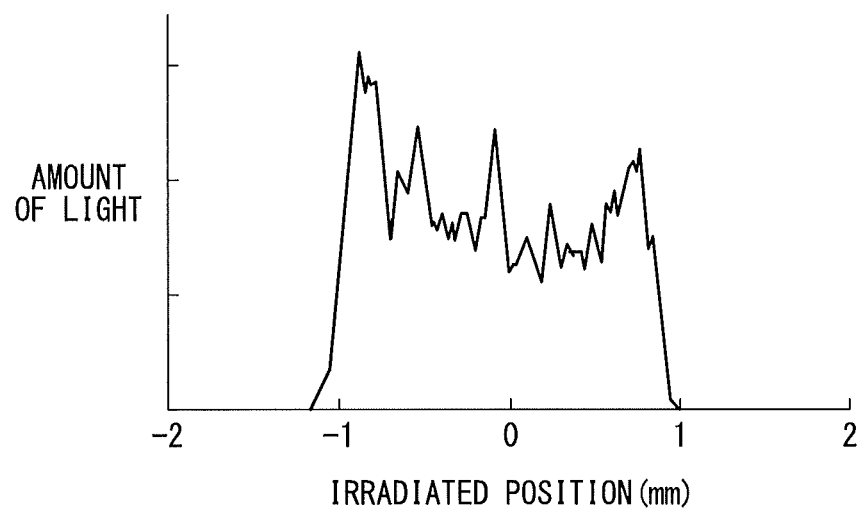
FIG. 12C is a graph showing the relationship between a range irradiated by the irradiation light shown in FIG. 11A and amounts of light.

Features of the measuring unit 50 according to the present embodiment will be described in detail in comparison with a conventional measuring unit 50'. FIGS. 11A and 11B are views schematically showing the manner in which measuring units 50, 50' apply irradiation light Li, FIG. 11A showing the manner in which the measuring unit 50 according to the present embodiment applies irradiation light Li and FIG. 11B showing the manner in which the conventional measuring unit 50' with an aperture 150 applies irradiation light Li'. FIGS. 12A and 12B are views showing the manner in which the irradiation lights Li, Li' shown in FIGS. 11A and 11B are applied, and FIGS. 12C and 12D are graphs showing the relationship between ranges irradiated by the irradiation lights Li, Li' and amounts of light.

As shown in FIG. 11B, in a conventional device wherein the measuring unit 50' has the aperture 150, the irradiation light Li' from an irradiation light lens 88a' is focused at a focal position P' that is closer to the irradiation light lens 88a' than a disposed position of a test paper 70'. The irradiation light Li' emitted by a light emitter 100' initially passes through the aperture 150, which changes the areas and shape of the irradiation light Li', and then is converged by the irradiation light lens 88a' and applied to the surface of the test paper 70'.

Figure 12D:
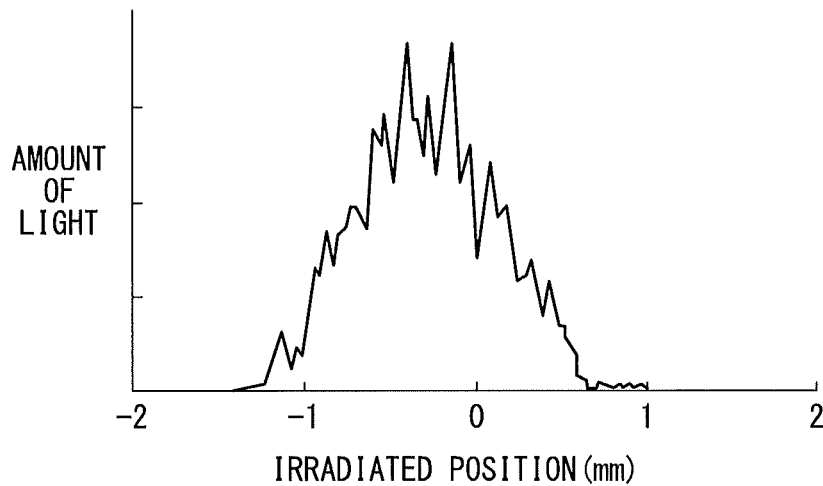
FIG. 12D is a graph showing the relationship between a range irradiated by the irradiation light shown in FIG. 11B and amounts of light.

If the focal position P' of the irradiation light lens 88a' is placed before the disposed position of the test paper 70', as shown in FIGS. 12B and 12D, the irradiation light Li' applied to the test paper 70' is more intensive at a center 202' of an irradiated range 200'. In other words, the irradiation light Li' applied to the test paper 70' has a centrally peaked intensity distribution such that its intensity is highest at the center 202' and progressively smaller toward an outer edge 204' of the irradiated range 200'. The outer edge 204' of the irradiated range 200' represents a blurred boundary because of a reduced intensity of the irradiation light Li'. Therefore, the measuring unit 50' measures a blood sugar level by detecting reflected light Lr' chiefly in the vicinity of the center 202' of the irradiated range 200'.

According to the present embodiment, as shown in FIG. 11A, the irradiation light Li is focused by the irradiation light lens 88a at a focal position P that is farther than the disposed position of the test paper 70. Specifically, the irradiation light lens 88a has a focal length (b+c) that is sufficiently longer than the distance b from the irradiation light lens 88a to the test paper 70. The irradiation light Li from the irradiation light lens 88a is applied to the surface of the test paper 70 in a dispersed state before it is focused at the focal position.

As shown in FIGS. 12A and 12C, the irradiation light Li applied to the test paper 70 has an intensity distribution that is relatively uniform in an irradiated range 200, or an intensity distribution such that its intensity is higher at an outer edge 204 of the irradiated range 200 than at a center 202 thereof. Therefore, it is possible to clearly distinguish between the irradiated range 200 that is irradiated with the irradiation light Li and the other range which is not irradiated with the irradiation light Li. Consequently, it is easy to aim at the colored area of the test paper 70 and it is possible to apply a constant amount of light to the colored area of the test paper 70.

Since the irradiation light lens 88a places the focal position P of the irradiation light Li farther than the test paper 70, the irradiation light lens 88a may comprise a lens having a large radius of curvature, i.e., a lens having a small curvature, or a thin lens. As the irradiation light lens 88a is thin, the measuring unit 50 may be reduced in size. As shown in FIG. 11A, the irradiation light lens 88a comprises a plano-convex lens in the present embodiment. However, the irradiation light lens 88a is not limited to a plano-convex lens, but may be a biconvex lens, a convex meniscus lens, or the like.

The light emitters 100 may comprise a general LED for emitting irradiation light Li having a measuring wavelength. The light emitters 100 are of a rectangular shape, i.e., a strip-like shape, because of a semiconductor fabrication process. Therefore, the irradiation light Li emitted from the light emitters 100 is of a substantially rectangular shape. However, inasmuch as the irradiation light path 108 has a cylindrical inner peripheral surface, the irradiation light Li that is applied to the test paper 70 is of a circular shape (see FIG. 12A).

When the test paper 70 is impregnated with the blood, the blood spreads radially from the position where the impregnation has started in the test paper 70.
Consequently, a circular impregnation area is usually formed in the test paper 70. As the circularly shaped irradiation light Li is applied to the test paper 70, the irradiation light Li can easily be brought within the impregnation area in the test paper 70. The blood can thus easily be measured within a certain range on the test paper 70.

As shown in FIG. 9, the measuring unit 50 according to the present embodiment includes the two light emitters, i.e., the first light emitter 100a and the second light emitter 100b, arranged at laterally juxtaposed positions, for emitting irradiation lights Li having different wavelengths to the single irradiation light lens 88a. Consequently, the spots on the test paper 70 which are irradiated with the first and second light emitters 100a, 100b are slightly displaced laterally on the test paper 70. However, since the focal position P of the irradiation light Li is farther than the disposed position of the test paper 70, any change in the spot diameter due to the displacement in the lateral direction is smaller than if the focal position P is placed before the test paper 70.

In as much as the single irradiation light lens 88a is provided with respect to the first and second light emitters 100a, 100b, the irradiation light lens 88a may have a large planar area in the measuring unit 50. The irradiation light lens 88a is thus capable of collecting an increased amount of the irradiation lights Li emitted from the first and second light emitters 100a, 100b and focusing them onto the test paper 70 for a higher accuracy of blood component measurement.

As shown in FIG. 8, the lens assembly 88 integrally includes, in addition to the irradiation light lens 88a, the reflected light lens 88b for focusing the reflected light Lr from the test paper 70 onto the light detector 102. As the irradiation light lens 88a and the reflected light lens 88b are integrally formed with each other, a process of positioning them is dispensed with at the time they are assembled, and the blood sugar level measuring device 10 is made up of a reduced number of parts and can be manufactured at a reduced cost.

Turning back to FIG. 11A, in the measuring unit 50 according to the present embodiment, the distance a from the light emitter 100 to the irradiation light lens 88a and the distance b from the irradiation light lens 88a to the test paper 70 are equal to each other. As a result, when the blood sugar level measuring device 10 is assembled, the worker can easily grasp shape errors and assembled states of various components, e.g., the distal case 20 and the photometric block 72, and adjust the two distances a, b appropriately for thereby reducing variations which may occur when individual blood sugar level measuring devices 10 are assembled. Even if shape errors and assembling errors occur, any adverse effects that shape and layout variations have on the irradiation light Li can be minimized by arranging the light emitters 100, the irradiation light lens 88a, and the test paper 70 at substantially equal intervals.

According to the present embodiment, the focal length (b+c) of the irradiation light lens 88a is sufficiently greater than the distance b from the irradiation light lens 88a to the test paper 70. Consequently, the angle θ between the irradiation light Li applied to the test paper 70 at the outer edge 204 and the test paper 70 is close to 90 degrees (see FIGS. 11A and 12A). The reflected light Lr that is reflected by the test paper 70 of the measuring unit 50 is divided into regularly reflected light (surface reflected light) essentially not including information about a blood component and diffused light including information about a blood component. The blood sugar level measuring device 10 detects the diffused light including information about a blood component, of the reflected light Lr, and measures a blood component from the detected diffused light.

As the angle θ between the irradiation light Li and the test paper 70 is of about 90 degrees, the regularly reflected light of the reflected light Lr travels at 90 degrees with respect to the test paper 70, i.e., travels toward the irradiation light lens 88a. On the other hand, only the diffused light of the reflected light travels to the reflected light lens 88b. Consequently, the measuring unit 50 detects only the diffused light for measuring a blood component with an increased accuracy.

Furthermore, since the focal position P of the irradiation light Li is farther than the disposed position of the test paper 70, when the blood sugar level measuring device 10 wobbles or the test paper 70 is positioned with an error, changing the distance b from the irradiation light lens 88a to the test paper 70, the amount of irradiation light Li changes gradually. In other words, the measuring unit 50 sees a change in the amount of irradiation light Li due to a change in the distance b, as proportional to a change in the area of the irradiated range 200.

As shown in FIG. 11B, when the focal point P' of the irradiation light lens 88a' is placed before the disposed position of the test paper 70', a rate of change of the area of the irradiated range 200' due to a change in a distance b' is large, resulting in a large change in the amount of light. On the other hand, as shown in FIG. 11A, when the focal position P of the irradiation light Li is farther than the disposed position of the test paper 70, a rate of change of the area of the irradiated range 200 due to a change in the distance b is small, resulting in a small change in the amount of light. As a consequence, even if the distance b changes, a stable amount of irradiation light Li is applied within a measuring range on the test paper 70 for a higher accuracy of blood component measurement.

Figure 13:
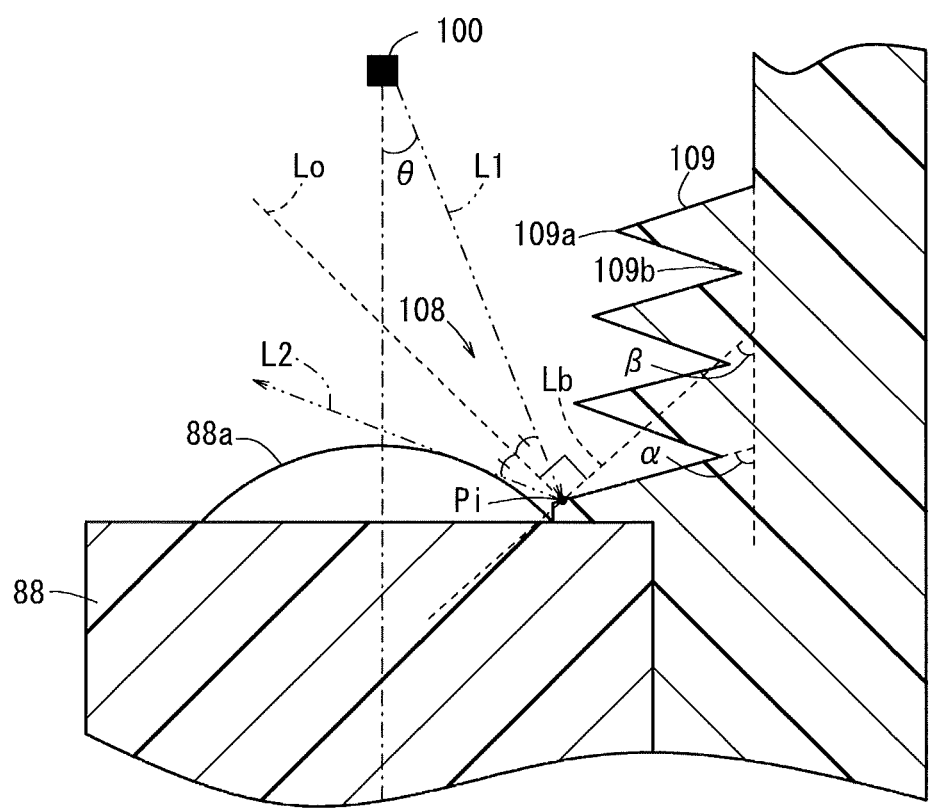
FIG. 13 is an enlarged cross-sectional view schematically showing an irradiation light path according to the embodiment.
Figure 14:
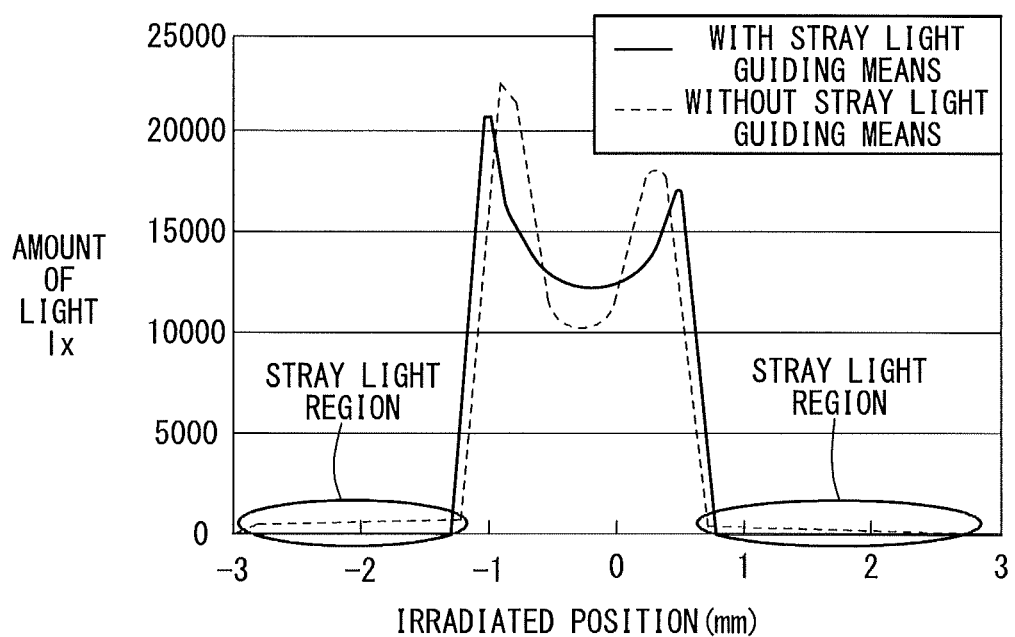
FIG. 14 is a graph showing the relationship between a range irradiated by the irradiation light in the irradiation light path shown in FIG. 13 and amounts of light.

FIG. 13 is an enlarged cross-sectional view schematically showing the irradiation light path 108 according to the present embodiment, and FIG. 14 is a graph showing the relationship between a range irradiated by the irradiation light Li in the irradiation light path 108 shown in FIG. 13 and amounts of light. As shown in FIG. 13, the measuring unit 50 according to the present embodiment includes a stray light guiding means 109 having ridges 109a and recesses 109b for guiding stray light SL out of the measuring range on the test paper 70.

According to the present invention, the stray light SL refers to light produced when the irradiation light Li emitted from the light emitter 100 is reflected even once by the inner peripheral surface of the irradiation light path 108. The stray light SL may be smaller in amount than the irradiation light Li emitted from the light emitter 100 and may have a wavelength different from the measured wavelength of the irradiation light Li. However, if the stray light SL is applied together with the irradiation light Li to the test paper 70 and included in the reflected light Lr from the test paper 70, then the measuring unit 50 detects noise such as flares, ghosts, etc. (see enclosed areas in FIG. 14). The stray light SL tends to occur if the aperture 150 is not present on the path of the irradiation light Li and the irradiation light Li spreads radially. In the case where the irradiation light path 108 extends all the way from the disposed position of the light emitter 100 to the disposed position of the irradiation light lens 88a according to the present embodiment, it is required to prevent adverse effects of the stray light SL from taking place. The stray light guiding means 109 has a function to prevent the stray light SL from being reflected.

As shown in FIG. 13, the stray light guiding means 109 according to the present embodiment is of a female screw configuration having an alternately successive array of the ridges 109a and the recesses 109b on the inner peripheral surface of the irradiation light path 108. The female screw configuration can be formed on the inner peripheral surface of the irradiation light path 108 by a male screw molding member, not shown, when the photometric block 72 is molded. Therefore, the photometric block 72 can easily be molded as it is not necessary to carry out a troublesome process such as a process of producing a complex mold for molding the photometric block 72.

The inner peripheral surface of the irradiation light path 108 is of a tapered shape that is progressively smaller in diameter toward the irradiation light lens 88a. Accordingly, after the irradiation light path 108 is molded into the female screw configuration, it can easily be removed from the mold simply by turning the male screw molding member. As a result, the process of molding the photometric block 72 can efficiently be performed. The stray light guiding means 109 is not limited to a female screw configuration or a tapered shape, but may be of a staircase shape having a plurality of steps or an array of ring-shaped ridges and grooves on the inner peripheral surface of the irradiation light path 108. Alternatively, the inner peripheral surface of the irradiation light path 108 may be coated with a light-absorbing material.

In designing the ridges and recesses (the stray light guiding means) 109, it is preferable that an angle α of the surface of each of the ridges 109a which faces the light emitter 100 with respect to the inner peripheral surface of the irradiation light path 108, for example, be an angle (gradient) for preventing the stray light SL from being applied to the irradiation light lens 88a. Specifically, the ridges and recesses 109 can be designed according to the following steps:

First, a straight line L1 is drawn which represents the irradiation light Li emitted from the light emitter 100 to the distal end of the ridge 109a of the ridges and recesses 109 which is closest to the irradiation light lens 88a (first step). Then, a tangential line L2 is drawn from a point Pi of intersection (the distal end of the ridge 109a) between the straight line L1 and the ridge 109a to the surface (curved surface) of the irradiation light lens 88a (second step). Thereafter, a central line Lo is drawn to bisect the angle formed between the straight line L1 and the tangential line L2 (third step). Finally, a reference line Lb is drawn perpendicularly to the central line Lo at the point Pi of intersection (fourth step).

In designing the ridges and recesses 109, the angle α is made greater than an angle β between the reference line Lb drawn as described above and the inner peripheral surface of the irradiation light path 108. Then, the irradiation light Li that is emitted from the light emitter 100 and applied to the ridges and recesses 109 is thus reflected in a direction away from the irradiation light lens 88a. Therefore, the possibility of the stray light SL being applied to the irradiation light lens 88a is greatly reduced, and the stray light SL will not be included in the reflected light Lr that is detected by the measuring unit 50.

As shown in FIG. 14, if the stray light guiding means 109 is dispensed with and the stray light SL is included in the reflected light Lr as indicated by the dotted-line curve in FIG. 14, then noise (stray light) representative of a small amount of light appears outside of the predetermined irradiated range that is irradiated with the irradiation light Li. On the other hand, in the case where the stray light guiding means 109 is provided and the stray light SL is not included in the reflected light Lr as indicated by the solid-line curve in FIG. 14, there is almost no amount of light outside of the irradiated range, thereby preventing noise from being produced. Therefore, the stray light guiding means 109 prevents the stray light SL from being included in the reflected light Lr detected by the measuring unit 50. The measuring unit 50 is thus capable of detecting a stable amount of reflected light Lr for accurately measuring a blood component on the test paper 70.

As described above, since the focal position P of the irradiation light Li is positioned farther than the disposed position of the test paper 70, the blood sugar level measuring device 10 can apply a stable amount of irradiation light Li within a predetermined range on the test paper 70 for a higher accuracy of blood component measurement. As there is no need for the aperture 150, the measuring unit 50 and the blood sugar level measuring device 10 can be reduced in size, and the blood sugar level measuring device 10 is made up of a reduced number of parts and can be manufactured at a reduced cost.

The present invention is not limited to the above embodiment, but may employ various arrangements without departing from the scope of the invention. For example, the component measuring device according to the present invention may be used as a device for measuring a urine component or a device for measuring a component in sewage, industrial water, or the like.

The invention claimed is:

1. A component measuring device including a measuring unit for applying measuring irradiation light through an irradiation light lens to an object to be measured and detecting reflected light from the object, a component in a liquid absorbed by the objected being measured based on the detected reflected light, wherein
    the irradiation light lens is included in the measuring unit such that, with respect to a disposed position of the irradiation light lens, a focal position of the irradiation light is beyond a disposed position of the object, a distance between the object and the focal position is longer than a distance between the irradiation light lens and the object, and a focal length of the irradiation light lens is longer than the distance between the object and the focal position,
    the measuring unit comprises:
    a light emitter for emitting the irradiation light;
    a light detector for detecting the reflected light;
    a board for supporting the light emitter and the light detector;
    a reflected light lens for focusing the reflected light onto the light detector; and
    a photometric block having an irradiation light path for disposing the light emitter so as to face the irradiation light lens; the irradiation light path extending from a disposed position of the light emitter to the disposed position of the irradiation light lens, and a reflected light path extending from a disposed position of the reflected light lens to a disposed position of the light detector,
    the photometric block further has a board placement region on its rear surface for placing the board, and the board placement region has a positioning projection extending through the board between the light emitter and the light detector for positioning the board, and configured to prevent light from directly propagating from the light emitter to the light detector.

2. The component measuring device according to claim 1, wherein the distance from the light emitter to the irradiation light lens is substantially equal to a distance from the irradiation light lens to the object.

3. The component measuring device according to claim 1, wherein the measuring unit comprises a plurality of the light emitters disposed so as to face the irradiation light lens.

4. The component measuring device according to claim 1, wherein the irradiation light lens is integrally formed with the reflected light lens.

5. The component measuring device according to claim 1, wherein the irradiation light path of the photometric block includes stray light guiding means for guiding stray light reflected by an inner peripheral surface of the irradiation light path out of a measuring range on the object through the irradiation light lens.

6. The component measuring device according to claim 5, wherein the inner peripheral surface of the irradiation light path is of a hollow cylindrical shape, and the stray light guiding means is of a female screw configuration.

7. The component measuring device according to claim 6, wherein the inner peripheral surface of the irradiation light path is of a tapered shape that is progressively smaller in diameter toward the irradiation light lens.

8. The component measuring device according to claim 5, wherein the stray light guiding means comprises an alternately successive array of a ridge and a recess on the inner peripheral surface of the irradiation light path, and an angle of the surface of the ridge which faces the light emitter is set to prevent the stray light from being applied to the irradiation light lens.

9. A component measuring device including a measuring unit for applying measuring irradiation light through an irradiation light lens to an object to be measured and detecting reflected light from the object, a component in a liquid absorbed by the objected being measured based on the detected reflected light, wherein the irradiation light lens is included in the measuring unit such that, with respect to a disposed position of the irradiation light lens, a focal position of the irradiation light is beyond a disposed position of the object, a distance between the object and the focal position is longer than a distance between the irradiation light lens and the object, and a distance between the irradiation light lens and the focal position is longer than the distance between the object and the focal position, the measuring unit comprises:

a light emitter for emitting the irradiation light;

a light detector for detecting the reflected light;

a board for supporting the light emitter and the light detector;

a reflected light lens for focusing the reflected light onto the light detector; and a photometric block having an irradiation light path for disposing the light emitter so as to face the irradiation light lens; the irradiation light path extending from a disposed position of the light emitter to the disposed position of the irradiation light lens, and a reflected light path extending from a disposed position of the reflected light lens to a disposed position of the light detector, the photometric block further has a board placement region on its rear surface for placing the board, and the board placement region has a positioning projection extending through the board between the light emitter and the light detector for positioning the board, and configured to prevent light from directly propagating from the light emitter to the light detector.

10. The component measuring device according to claim 9, wherein the distance from the light emitter to the irradiation light lens is substantially equal to a distance from the irradiation light lens to the object.

11. The component measuring device according to claim 9, wherein the measuring unit comprises a plurality of the light emitters disposed so as to face the irradiation light lens.

12. The component measuring device according to claim 9, wherein the irradiation light lens is integrally formed with the reflected light lens.

13. The component measuring device according to claim 9, wherein the irradiation light path of the photometric block includes stray light guiding means for guiding stray light reflected by an inner peripheral surface of the irradiation light path out of a measuring range on the object through the irradiation light lens.

14. The component measuring device according to claim 13, wherein the inner peripheral surface of the irradiation light path is of a hollow cylindrical shape, and the stray light guiding means is of a female screw configuration.

15. The component measuring device according to claim 14, wherein the inner peripheral surface of the irradiation light path is of a tapered shape that is progressively smaller in diameter toward the irradiation light lens.

16. The component measuring device according to claim 13, wherein the stray light guiding means comprises an alternately successive array of a ridge and a recess on the inner peripheral surface of the irradiation light path, and an angle of the surface of the ridge which faces the light emitter is set to prevent the stray light from being applied to the irradiation light lens.

* * * * *